United States Patent [19]

Davidson et al.

[11] Patent Number: 5,565,980
[45] Date of Patent: Oct. 15, 1996

[54] APPARATUS FOR THE DETECTION OF SURFACE DEFECTS

[75] Inventors: Iain S. Davidson; Thomas G. Rice; Mark Hague, all of Preston, United Kingdom

[73] Assignee: British Nuclear Fuels plc, Cheshire, United Kingdom

[21] Appl. No.: 360,838

[22] PCT Filed: May 3, 1994

[86] PCT No.: PCT/GB94/00940

§ 371 Date: Jan. 3, 1995

§ 102(e) Date: Jan. 3, 1995

[87] PCT Pub. No.: WO94/25858

PCT Pub. Date: Nov. 10, 1994

[30] Foreign Application Priority Data

May 5, 1993 [GB] United Kingdom .................. 9309238

[51] Int. Cl.⁶ ............................................... G01N 21/48
[52] U.S. Cl. ........................... 356/237; 356/426; 376/248
[58] Field of Search ............................. 356/237, 73, 445, 356/426, 446, 371; 250/562, 563, 572, 559.39, 559.45, 559.22, 559.46, 223 R; 209/587, 579, 538; 376/245, 248, 261

[56] References Cited

U.S. PATENT DOCUMENTS

| | | | |
|---|---|---|---|
| 4,002,823 | 1/1977 | Van Oosterhout | 356/240 |
| 4,162,126 | 7/1979 | Nakagawa et al. | 356/430 |
| 4,226,539 | 10/1980 | Nakagawa et al. | 356/445 |
| 4,410,278 | 10/1983 | Makihira et al. | 356/445 |
| 4,532,723 | 8/1985 | Kellie et al. | 356/73 |
| 5,147,047 | 9/1992 | Ahmed et al. | 356/426 |
| 5,186,887 | 2/1993 | Yaginuma | 376/248 |
| 5,309,486 | 5/1994 | Lichauer et al. | 376/248 |
| 5,426,309 | 6/1995 | Davidson et al. | 356/237 |

Primary Examiner—Hoa Q. Pham
Attorney, Agent, or Firm—Nixon & Vanderhye P.C.

[57] ABSTRACT

An apparatus for the detection of surface defects on cylindrical objects which includes means for conveying the objects to be inspected one-by-one each on its end to a first inspection station, means for inspecting the free end of each object as it passes through the first inspection station, means for conveying the objects one-by-one each on its side to a second inspection station the means for tipping the objects from their ends to their sides, means for rotating each object whilst passing it on its side through the second inspection station, means for inspecting the curved surface of each object as it passes through the second inspection station, means for conveying the objects one-by-one to a third inspection station the said means including means for tipping the objects onto their end inspected at the first inspection station and means for inspecting the free end of each object as it passes through the third inspection station.

11 Claims, 2 Drawing Sheets

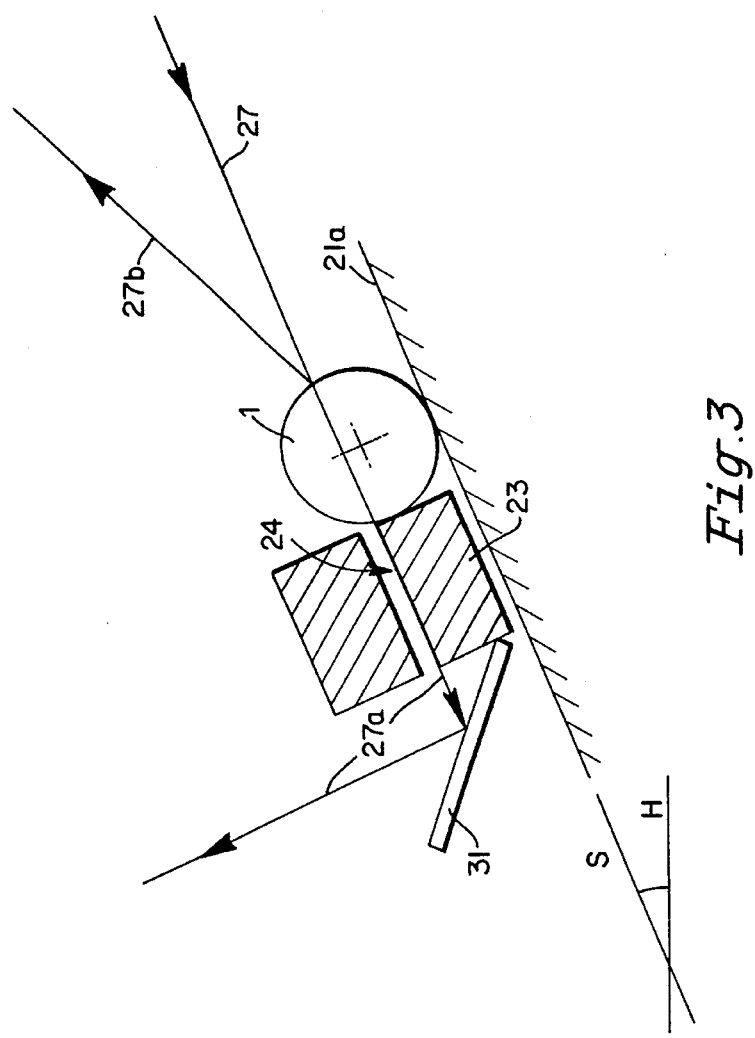
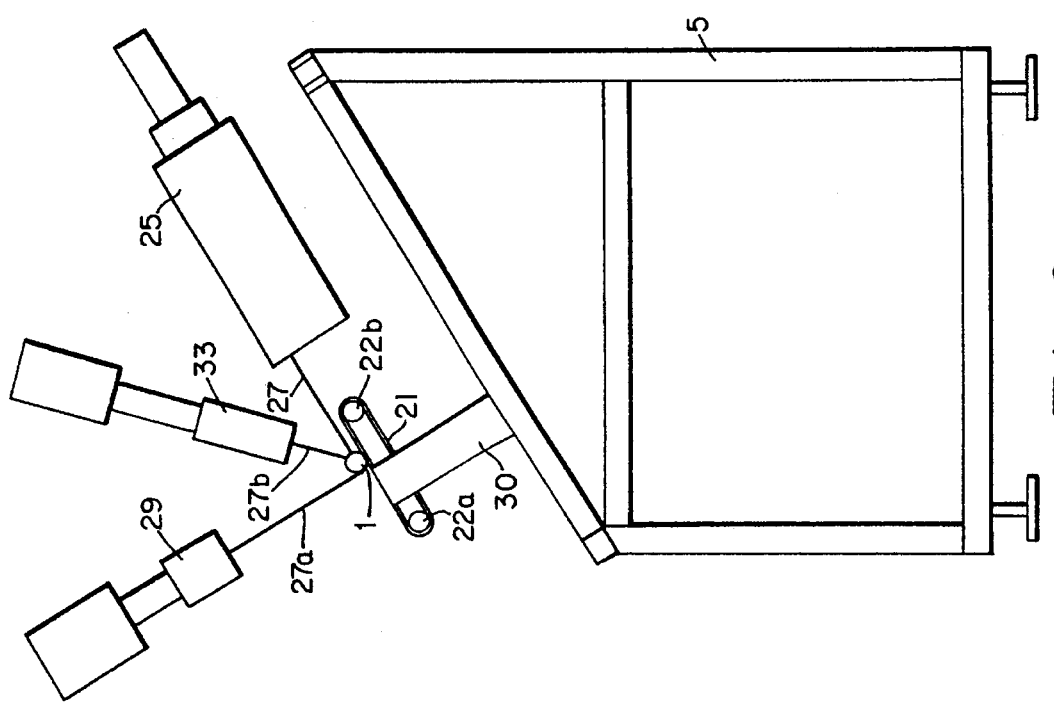

APPARATUS FOR THE DETECTION OF SURFACE DEFECTS

BACKGROUND OF THE INVENTION

1. Field of the Invention

The present invention relates to apparatus for the detection of surface defects especially on cylindrical objects such as nuclear fuel pellets.

2. Discussion of Prior Art

Certain cylindrical objects such as nuclear fuel pellets have to meet very demanding manufacturing quality specifications. Such objects may be manufactured by an automated manufacturing route without handling by human operators and in such a route it will be necessary to inspect the objects for surface defects using automatic apparatus. The objects may for example be sintered cylindrical $UO_2$ (uranium dioxide) pellets for a so-called "agr" fuel element. Such pellets have an axial hole or bore provided for fuel performance reasons. The sintered pellets are inserted in stainless steel cladding tubes, the tubes being sealed to form a fuel pin and a cluster of pins being assembled to form fuel elements. The pellets require automatic inspection before insertion in the cladding tubes.

SUMMARY OF THE INVENTION

According to the present invention there is provided an apparatus for the detection of surface defects on cylindrical objects which includes means for conveying the objects to be inspected one-by-one each on its end to a first inspection station, means for inspecting the free end of each object as it passes through the first inspection station, means for conveying the objects one-by-one each on its side to a second inspection station the means including means for tipping the objects from their ends to their sides, means for rotating each objects whilst passing it on its side through the second inspection station, means for inspecting the curved surface of each object as it passes through the second inspection station, means for conveying the objects one-by-one to a third inspection station the said means including means for tipping the objects onto their end inspected at the first inspection station and means for inspecting the free end of each object as it passes through the third inspection station.

Unlike prior art systems the apparatus according to the present invention allows all surfaces excepting the surface in the bore if present of the cylindrical objects to be inspected in a continuous operation the objects being presented one-by-one to the apparatus by a conveying means.

The present invention is particularly applicable to the automatic inspection of nuclear fuel pellets. The pellets may comprise well known shapes, e.g. they may be hollow or solid right circular substantially cylindrical bodies. The ends may be flat surfaces or may be convex curves rather than flat surfaces. The pellets may for example be for use in either so called AGR or LWR types of nuclear reactor. The pellets may comprise uranium oxide optionally doped with one or more known additives, e.g. niobia or gadolinia. Alternatively, the pellets may comprise MOX (mixed oxide fuel) e.g. comprising a mixture of uranium and plutonium oxides. In that case, the pellets will normally be within a containment such as a glovebox which confines the plutonium oxide thereby preventing outside contamination. The components of the apparatus according to the invention may be located outside such containment. The containment may include a window, e.g. made of a high quality glass, which allows the optical radiation to pass in and out of the containment to inspect the pellets therein. As only a small number of pellets need to be in the containment for inspection at any one time the window is not required to act as a radiation shield. Conventional neutron and gamma radiation shielding material can be provided around the components of the apparatus located outside the containment containing the pellets being inspected.

The means for tipping the objects between the first and second inspection stations may include a first tipping station comprising a step on the conveying track the step changing the attitude of the axes of the objects from vertical to horizontal. The means for tipping the objects between the second and third inspection stations may include a second tipping station comprising shaped step on the conveying track the step changing the attitude of the axes of the objects from horizontal to vertical. The conveying track after the first tipping station may include a blocking bridge which blocks objects remaining in the vertical attitude after the first tipping station.

Desirably, the means for inspecting the curved surface comprises means for scanning an optical beam along the objects when at the second inspection station and first detector means for detecting a reflected beam comprising reflections of the scanned beam by each translating and rotating cylindrical object inspected by the scanned beam.

The optical beam may be a laser beam in the visible or other part of the spectrum.

The signal detected in use by the first detector means will be significantly reduced owing to the scattering of the incident optical beam when a defect is present on the inspected surface and such reduction therefore provides information about the presence of a surface defect. The defect may be a chip or crack or scratch or stain or it may be a roughened surface area which has not been smoothed during manufacture. The dimensions of such a defect, e.g. length, width and surface area may be measured by monitoring the duration of the reduction or reductions (if periodic during the rotation of the object) of the detected signal. The value of these periods may be digitised and compared in a signal processor with one or more reference values to determine whether one or more of the dimensions of the defect or its areas exceeds a pre-determined acceptable limit.

The means for inspecting the curved surface may additionally include a second detector means for detecting a transmitted beam comprising transmission of the scanned beam when it does not impinge upon the object. The transmitted beam may be directed onto the second detector means by one or more mirrors. The detection of a signal by the second detector means indicates that the scanned beam has traversed the path of the inspected object at a location beyond the end of the object. The signal is significantly reduced when the scanned beam is incident on the object, ie represents a shadow cast by the object. Monitoring of the duration of the reduction of the signal therefore provides measure of the position and length of the object. The duration of the reduction of the signal may be converted in a signal processor with a digital value and compared with a pre-determined reference value. If the measured duration is too long or too short it indicates that the object has an incorrect length or has a defect adjacent to its end surface, e.g. across its end and curved surfaces. It may also be desirable to measure the difference between the duration of the signal detected by the first detector means and the duration of the signal detected by the second detector means.

If the difference (which is likely to vary as the object is rotating) is too great the object may be rejected. The signal processor which processes the output of the first and second detector means may be a single common processor. The processor may produce a "fail" or "pass" signal to indicate whether the object inspected has or has not unacceptable surface defects.

The means for rotating each object whilst passing on its side through the second inspection station may comprise a continuous belt and means for moving the belt over two spaced apart guides, e.g. rollers, one guide being at a higher vertical position than the other whereby the upper surface of the belt is inclined relative to the vertical and horizontal axes, and a guide bar running close to and across the upper surface of the belt, whereby when objects are positioned on the belt immediately above the guide bar they traverse the belt in contact with the guide bar whilst being rotated on their own axis by the movement of the belt. This transverse motion is caused by the belt angle.

The means for inspecting the free end of each object at the first inspection station and at the third inspection station may comprise a gauge which capacitively senses the gap between the gauge and the object as the object passes the gauge e.g. as described in Patent No. GB 2145231. Where the gap at any location on the end is increases or reduced by the presence of an end surface defect the signal detected is reduced or increased accordingly. The gauge therefore enables the depth and also the length, width and area of defects to be measured by monitoring deviations in the detected signal from the norm obtained for a defect-free end surface of the object. The gauge may include a signal processor which, in a manner similar to the aforementioned signal processor, compares a signal representing the dimensions of a detected defect with one or more given reference signals and produces a "pass" or "fail" signal.

Where an unacceptable defect on the surface of an inspected object is detected at any one of the first, second and third inspection stations the object may be removed from the procession of objects being considered, e.g. by a reject station after each inspection station which comprises a pusher, e.g. operated pneumatically under control of an output "fail" signal from the signal processor of the inspection means, which is arranged to push the defective objects onto a reject track.

The apparatus may be calibrated in use from time-to-time by presenting a dummy object having surface defects of known dimensions to the inspection stations.

The first, second and third inspection stations may each include one or more means for detecting the presence of an object close to the means for inspecting the end surface, e.g. an optical proximity sensor, providing an output signal to energise the means for inspection whereby that means is energised only when the object is at the inspection station.

The means for inspecting each free end of the objects may alternatively be an apparatus as claimed in Applicant's copending EP Patent Application No. 588624A the contents of which are deemed to be incorporated herein be reference. Such an apparatus comprises means for irradiating the end surface of the object, detector means for detecting radiation reflected by the end surface substantially parallel to the axis of the object and calculator means for calculating the proportion of the end surface which has reflected radiation directly to the detector means.

The principle underlying the apparatus the subject of EP 588624A is that the end surface will reflect radiation to the detector means to an extent which depends upon the texture of the surface. Where the surface is a smooth defect-free surface reflection of radiation by the surface is predominantly specular, ie close to the axis normal to surface the reflecting surface. Where the end surface includes a defect, e.g. a crack or chip, the reflection of radiation by the defect is diffuse; the intensity of defect is low. By locating the detector means substantially on the axis of the object the detection by the detector means of low intensity specular reflection due to defects is possible. The means for irradiating may comprise a ring light source the centre of the ring being substantially co-incident with the axis of the object and being substantially transparent to reflected radiation so that light reflected to the detector means passes unhindered through the ring light. The means for irradiating may comprise a plurality of ring light sources each having its ring centre substantially coincident with the axis of the object at different positions along the axis. The light reaching the detector means needs to pass unhindered through all of the light rings. The detector means desirably comprises an electronic imaging photo-detector; although it may alternatively comprise a non-imaging photo-detector. In the case of the non-imaging photo-detector, the output signal is proportional to the total amount of light incident on the detector, light received by the photo-detector coming substantially from the object end. In the case of the imaging photo-detector, the output signal from the detector means comprises components representing reflected radiation intensities detected by the detector means from different elements of the object surface.

In the case of the imaging photo-detector in the apparatus of EP 588624A, the calculator means may comprise a signal processor which analyses the output signal provided by the detector means. Such a processor may sum all the signal components magnitudes and compare the summation with a pre-determined reference level. The calculation means may also be an image processor which analyses the output signal provided by the detector means. Such a processor may compare the output component magnitudes with a pre-determined reference level. The processor thereafter counts the number of components or pixels which have a signal magnitude (intensity, in terms of the image) respectively above and below the reference level. The number of pixels above the reference level will be representative of the area of the object that is undamaged.

The main procession of objects in use of the apparatus according to the present invention may be a Cushion Transfer (RTM) conveyer which is a conveyer having a conveying track surface of the type described and claimed in UK Patent No. GB 2223998B. The form of the conveying surface may be flat before the first tipping station and after the second tipping station and may be of V-shaped or U-shaped section to guide the objects in the region between the first and second tipping stations.

There may be a queue sensor device on the conveying track before each of the said inspection stations. Each queue sensor may have an escapement mechanism which releases objects in the queue a given distance apart so that when they pass through the inspection station there is no mutual interference between the objects being inspected.

At the entry to the first and third inspection stations the conveying track may bias the objects against a datum face so that they are in the correct lateral position (relative to the axis of the conveying track) when being inspected.

BRIEF DESCRIPTION OF THE DRAWINGS

Embodiments of the present invention will now be described with reference to the accompanying drawings, in which:

FIG. 2 is cross-sectional end view on the line II—II in FIG. 1;

FIG. 3 is an enlargement showing more detail of part of the arrangement of FIG. 2.

DETAILED DISCUSSION OF PREFERRED EMBODIMENTS

Figure 1:
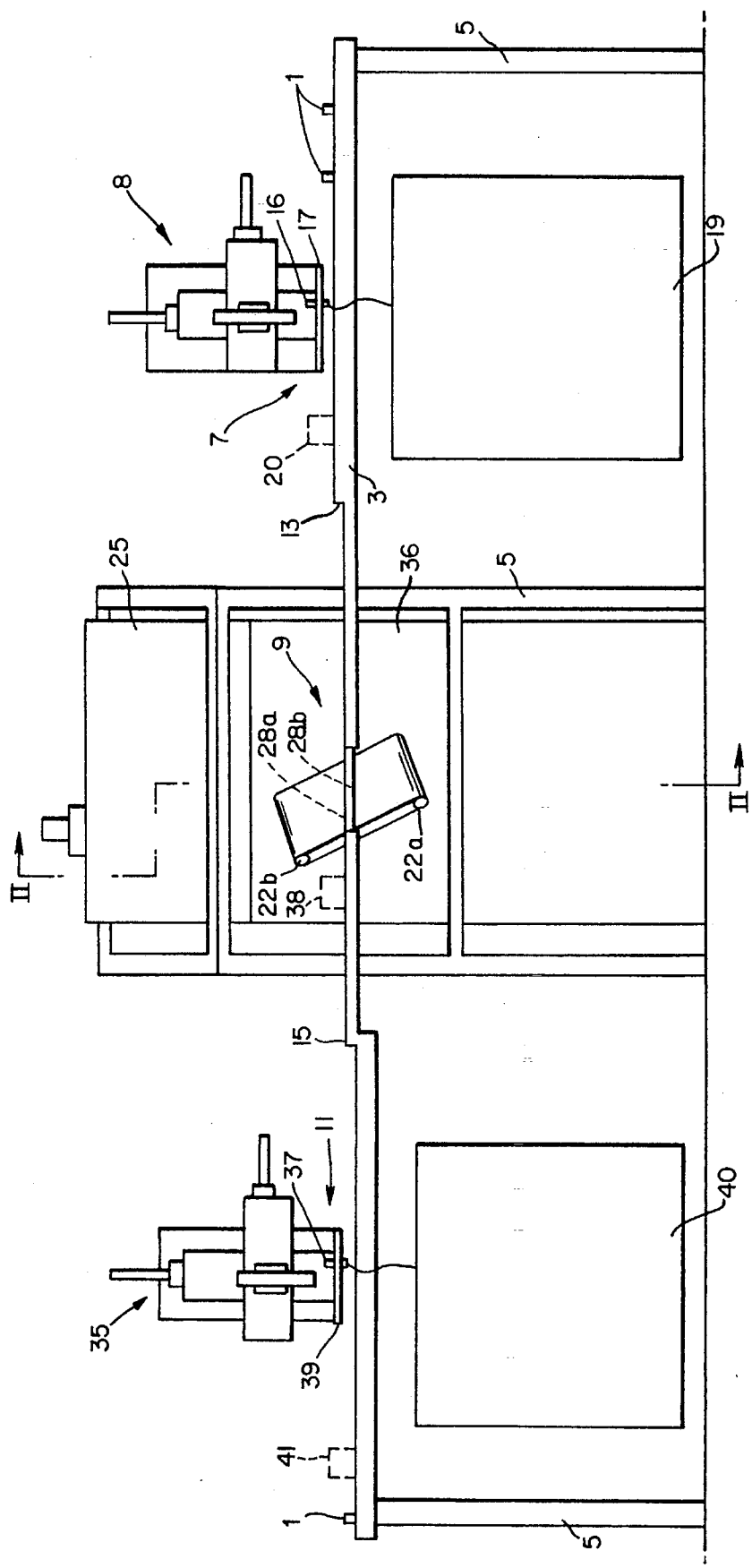
FIG. 1 is a side elevation of an inspection apparatus embodying the present invention.

In FIGS. 1–3, nuclear fuel pellets 1, e.g. cylindrical $UO_2$ sintered pellets for an agr fuel, are checked for surface defects by the apparatus shown in the drawings. The pellets 1 are transported on a conveyor 3 having a Cushion Transfer (RTM) upper surface. The conveyor 3 is mounted on a support structure 5. The conveyor 3 transports the pellets 1 successively to a first inspection station 7, a second inspection station 9 and a third inspection station 11. Tipping stations 13, 15 comprising shaped steps on the conveyor 3 cause the attitude of the axes of the pellets 1 to change respectively from vertical to horizontal and from horizontal to vertical.

The first inspection station 7 comprises an end inspection gauge 8 which inspects one end surface of the pellets 1. An optical proximity sensor 16 senses the presence of the pellet 1 and energises the gauge 8 for inspection. The gauge 8 is of the kind described in patent specification no. GB 2145231. An inspection gauge head 17 measures capacitively the gap (normally 1 mm) between the head 17 and the inspected surface of the pellet 1 when it passes under the head 17. If the pellet surface contains a defect the measured capacitance deviates from an expected norm and the deviation is recorded and digitised by a signal processing unit 19. Where a defect is detected and the dimensions of the defect are by comparison with stored reference values, found to be unacceptable, the unit 19 provides an output signal to a reject station where a pneumatically operated pusher (not shown) causes the pellet to be pushed into a reject track on the side of the main conveyor 3.

The pellets 1 which have not been rejected after inspection at the first inspection station 7 are tipped onto their side, ie so that their axes are horizontal, by the tipping station 13. The pellets 1 are next presented to the second inspection station 9 at which the side curved surface of each pellet 1 is inspected. At the second inspection station 9 each pellet travels through the station from right to left as shown in FIG. 1 whilst rotating on its own axis. Each pellet 1 is presented to a continuously moving belt 21 which passes over rollers 22a, 22b supported on a frame 30. As seen in FIGS. 2 and 3 the roller 22b is at a vertically higher position than the roller 22a whereby the belt 21 moves along a surface in a plane indicated by S in FIG. 3 which is at an angle of about 30 degrees to the horizontal plane indicated by H in FIG. 3. A guide bar 23 is located close to and across the upper surface 21a of the belt 21 as shown in FIG. 3 whereby the pellets 1 are allowed to slip against the guide bar 23 and grip the belt 21 whereby they are caused to traverse the belt 21.

The second inspection station includes a scanning laser device 25 also mounted on the structure 5 (as seen in FIG. 1) which scans an incident laser beam 27 along the path of the pellet 1 whilst being translated and rotated. The laser beam 27 scan extends between positions indicated by dashed lines 28a and 28b in FIG. 1 which have a separation greater than the length of the pellets 1. When the beam 27 is not incident on the pellet 1 it is transmitted as a transmitted beam 27a and is then detected by a transmitted beam detector 29 (shown in FIG. 2 but not in FIG. 1). The transmitted beam 27a passes through a passage 24 in the guide plate 23 and is reflected by a mirror 31 onto the transmitted beam detector 29.

When the laser beam 27 is incident on the pellet 1 it is reflected as a reflected beam 27b onto a reflected beam detector 33 (shown in FIG. 2 but not in FIG. 1).

The signal detected by the detector 29 allows the length and position of the pellet to be detected. If the pellet 1 is too long or too short it is rejected. No signal is produced at the receiver 29, ie the receiver looks at a shadow whilst the beam 27 reflects as the reflected beam 27b at the pellet 1. If the pellet 1 contains an "end cap" across its end and side surfaces the measured length obtained by comparing the output of the detector 29 with the output of the detector 33 will appear to deviate from a known norm during its rotation on the belt 21 and the pellet may be recorded as defective. If the pellet 1 contains a scratch or other defect on its curved side surface the laser beam 27 will be scattered by the defect and the signal detected by the reflected beam detector 33 will be significantly reduced. The dimensions of the defect may be measured by feeding the output of the detector 33 to the processor 36 and there digitising the value of the duration of the scattering of the beam 27 whilst the pellet 1 is translating and rotating and comparing the digitised value with pre-determined reference values. Defects on the curved surface which are found in this way to be greater than a pre-determined length and/or a pre-determined area may be deemed unacceptable. A reject station (not shown) controlled by outputs from the processor 36 causes separation of the defective pellets 1 before inspection at the third inspection station 11. This reject station may comprise an opening in the guide bar 23 which is covered by a cover which is removable when actuated.

The pellets 1 which have not been rejected after inspection at the second inspection station 9 are tipped onto their end (opposite to that on which they were inspected at the first station 7), ie so that their axes are vertical, by the tipping station 15. The pellets 1 are then presented to the third inspection station 11 which comprises an inspection gauge 35 which is the same as the gauge 8, ie has an optical proximity sensor 37 similar to the sensor 16, a capacitive inspection gauge head 39 similar to the head 17 and a signal processing unit 40 similar to the unit 19. When unacceptable defects are detected by the unit 40, the unit 40 operates a mechanism (similar to that of the reject station 21) at a reject station 41. Finally, acceptable pellets 1 reach the end of the conveyor 3 (at the left as shown in FIG. 2) and may subsequently be transferred to a buffer store (not shown) or to the next stage of the manufacturing route.

The parts of the apparatus shown in the drawings which convey, collect or store pellets 1 (including rejects) may be contained within a safety enclosure having a controlled atmosphere and filter system to capture airborne radioactive particles.

We claim:

1. An apparatus for the detection of surface defects on cylindrical objects which includes means for conveying the objects to be inspected one-by-one each on its end to a first inspection station, means for inspecting the free end of each object as it passes through the first inspection station, means for conveying the objects one-by-one each on its side to a second inspection station the means including means for tipping the objects from their ends to their sides, means for rotating each objects whilst passing it on its side through the second inspection station, means for inspecting the curved surface of each object as it passes through the second inspection station, means for conveying the objects one-by-one to a third inspection station the said means including means for tipping the objects onto their end inspected at the first inspection station and means for inspecting the free end of each object as it passes through the third inspection station.

2. Apparatus as in claim 1 and wherein the means for tipping the objects between the first and second inspection stations includes a first tipping station comprising a step on the conveying means the step being adapted change the attitude of axes of the objects from vertical to horizontal and the means for tipping the objects between the second and third inspection stations includes a second tipping station comprising a shaped step on the conveying means the step being adapted to change the attitude of the axes of the objects from horizontal to vertical.

3. Apparatus as in claim 1 and wherein the means for inspecting the curved surface comprises means for scanning an optical beam along the objects when at the second inspection station and first detector means for detecting a reflected beam comprising reflections of the scanned base by each translating and rotating cylindrical object inspected by the scanned beam.

4. Apparatus as in claim 3 and including a signal processor for comparing the signal detected by the first detector means with a reference signal.

5. Apparatus as in claim 1, and wherein the means for inspecting the curved surface additionally includes a second detector means for detecting a transmitted beam comprising transmission of the scanned beam when it does not impinge upon the object.

6. Apparatus as in claim 5 and including at least one mirror to direct the transmitted beam onto the second detector means.

7. Apparatus as in claim 5 and wherein the signal processor is also adapted to compare the signal by the second detector means with a reference signal.

8. Apparatus as in claim 1 and wherein the means for rotating each object whilst passing on its side through the second inspection station comprises a continuous belt and means for moving the belt over two spaced apart guides, one guide being at a higher vertical position than the other whereby the upper surface of the belt is inclined relative to the vertical and horizontal axes, and a guide bar running close to and across the upper surface of the belt, whereby when objects are positioned on the belt immediately above the guide bar they traverse the belt in contact with the guide bar whilst being rotated on their own axis by the movement of the belt.

9. Apparatus as in claim 1 and wherein the means for inspecting the free end of each object at either or both of the first inspection station and the third inspection station comprises a gauge which capacitively senses the gap between the gauge and the object as the object passes the gauge.

10. Apparatus as in claim 1 and wherein at least one of the means for inspecting the free end of each object and the means for inspecting the curved surfaces of each object includes means for irradiating at least one surface of the object, detector means for detecting radiation reflected by said at least one surface and calculator means for calculating the proportion of the surface which has reflected radiation directly to the detector means.

11. Apparatus as in claim 1 and wherein at least one of the first, second and third inspection stations includes at least one means for detecting the presence of an object close to the inspection station providing in use an output signal to energise the means for inspection whereby that means is energised only when the object is at the inspection station.

* * * * *